United States Patent [19]

Mack

[11] Plant 4,491

[45] Jan. 8, 1980

[54] CHRYSANTHEMUM PLANT

[76] Inventor: Grace H. Mack, 108 Wahackme Rd., New Canaan, Conn. 06840

[21] Appl. No.: 833,375

[22] Filed: Sep. 14, 1977

[51] Int. Cl.[2] ..... A01H 5/00

[52] U.S. Cl. ..... Plt./75

[58] Field of Search ..... Plt./75, 82

*Primary Examiner*—Robert E. Bagwill

*Attorney, Agent, or Firm*—Donald D. Jeffery

[57] ABSTRACT

A chrysanthemum cultivar particularly characterized as to uniqueness by the combined characteristics of flat capitulum form, pompon capitulum type, red-bronze ray floret color, diameter across face of capitulum up to 40 mm., short plant height, spreading branching pattern, average natural season flowering date of September 27, and average flowering response period of seven weeks in photoperiodic controlled short day programs.

6 Drawing Figures

The present invention comprises a new and distinct cultivar of *Chrysanthemum morifolium,* Ramat., hereinafter referred to by the cultivar name Bandit (#21750E48).

Bandit is a product of a planned breeding program which had the objective of creating cultivars with pompon capitulum type, short height, spreading branching pattern, durable inflorescence, short (six to seven week) flowering response period, and bronze ray floret color under outdoor natural season conditions.

Bandit was originated from a cross made in a controlled breeding program in New Canaan, Conn. in the year 1972. The male parent was C-1-70 (#21730E13; unnamed seedling). The female parent was #69058M01 (unnamed seedling).

Bandit was discovered and selected as a flowering plant within the progeny of the stated cross by Grace H. Mack in September, 1973 in an outdoor field in New Canaan, Conn. The first act of asexual reproduction of Bandit was accomplished when vegetative cuttings were taken from the initial selection in May, 1974 in New Canaan, Conn. by Grace H. Mack. Horticultural examination of selected units initiated Oct. 6, 1975 has demonstrated that the combination of characteristics as herein disclosed for Bandit are firmly fixed and are retained through successive generations of asexual reproduction.

Bandit has not been observed under all possible environmental conditions. The phenotype may vary significantly with variations in environment such as temperature, light intensity, and day length. The following observations, measurements, and comparisons describe plants grown in a field in Barberton, Ohio under conditions which are generally described in *Local Climatological Data, Annual Summary With Comparative Data,* Akron, Ohio, U.S. Department of Commerce, National Oceanic and Atmospheric Administration, Environmental Data Service, Washington, D.C. 1975, 1976, and *Tables of Sunrise, Sunset, and Twilight.* Supplement to the American Emphermeris, 1946, U.S. Naval Observatory, Washington, D.C., pg. 103.

The following traits have been repeatedly observed and are determined to be basic characteristics of Bandit which in combination distinguish this chrysanthemum as a new and distinct cultivar:

(1) Flat capitulum form.
(2) Pompon capitulum type (commercial double).
(3) Red-bronze ray floret color.

(4) Diameter across face of capitulum up to 40 mm.
(5) Short plant height (requiring 2–3 long day weeks prior to short days and 1 application of 2500 ppm B9-SP to attain a flowered plant height of 30 to 35 cm.).
(6) Spreading branching pattern.
(7) Average natural season flowering date of September 27.
(8) Average flowering response period of 7 weeks in photoperiodic controlled flowering programs.

The accompanying photographic drawings show typical inflorescence and foliage characteristics of Bandit. Some degree of difficulty was encountered in obtaining accurate color representation in the photographic drawing of Bandit. The actual ray floret color of Bandit is less yellow, and therefore, less vibrant than that depicted in the color photograph. The color values stated below are, however, correct. Sheet 1 is a color photograph of Bandit. Sheet 2 is a black and white photograph showing three views of the inflorescence of Bandit. Sheet 3 is a black and white photograph showing the foliage of Bandit at three stages of growth.

Of the many commercially available cultivars known to the present inventors, the most similar existing cultivar in comparison to Bandit is the unpatented cultivar Brown Eyes (#21660E12).

Reference is made to attached Chart A which compares certain characteristics of Bandit with the same characteristics of Brown Eyes. It will be noted that in comparison to Brown Eyes, Bandit has different ray floret color, earlier average natural season flower date, and smaller diameter across face of capitulum. The capitulum form, capitulum type, plant height, branching pattern, and plant spread of Bandit are similar to those of Brown Eyes.

In the following description, color references are made to The Munsell Limit Color Cascade, 1972 edition. The color values were determined between 8:30 and 9:00 A.M. on May 13, 1977 under 150 foot-candle light intensity at Barberton, Ohio.

BOTANICAL CLASSIFICATION: *Chrysanthemum morifolium,* Ramat., cv Bandit.

I. INFLORESCENCE

A. Capitulum:

*Form.*—Flat.

*Type.*—Pompon (commercial double).

*Permanence.*—14–21 days.

*Diameter across face.*—35 to 40 mm.

B. Corolla of Ray Floret:

*Color (abaxial).*—36-15 to 34-14.

*Color (adaxial).*—33-13 over 28-5 but more greyed.

C. Reproductive Organs:

*Androecium.*—Present disc florets; scant pollen.

*Gynoecium.*—Present both ray and disc florets.

CHART A

COMPARISON OF BANDIT AND BROWN EYES

| CULTIVAR | RAY FLORET COLOR | CAPITULUM FORM AND TYPE | AVERAGE NATURAL SEASON FLOWER DATE |
|---|---|---|---|
| BANDIT | Red-bronze | Flat Pompon | September 27 |
| BROWN EYES | Copper-bronze | Flat Pompon | October 5 |

| | PLANT | BRANCHING PATTERN AND | DIAMETER ACROSS FACE OF |
|---|---|---|---|

CHART A-continued

COMPARISON OF BANDIT AND BROWN EYES

| CULTIVAR | HEIGHT | SPREAD | CAPITULUM |
|---|---|---|---|
| BANDIT | Short, from 20 to 25 cm. | Spreading from 35 to 40 cm. | 35 to 40 mm. |
| BROWN EYES | Short, from 20 to 25 cm. | Spreading from 35 to 40 cm. | 45 to 60 mm. |

COMPARISONS MADE OF PLANTS GROWN UNDER NATURAL SEASON OUTDOOR FIELD CONDITIONS IN BARBERTON, OHIO.

I claim:

1. A new and distinct cultivar of *Chrysanthemum morifolium,* Ramat. plant known by the name Bandit and particularly characterized as to uniqueness by the combined characteristics of flat capitulum form, pompon capitulum type (commercial double), red-bronze ray floret color, diameter across face of capitulum up to 40 mm., short plant height, spreading branching pattern, average natural season flowering date of September 27, and average flowering response period of seven weeks in photoperiodic controlled short day programs.

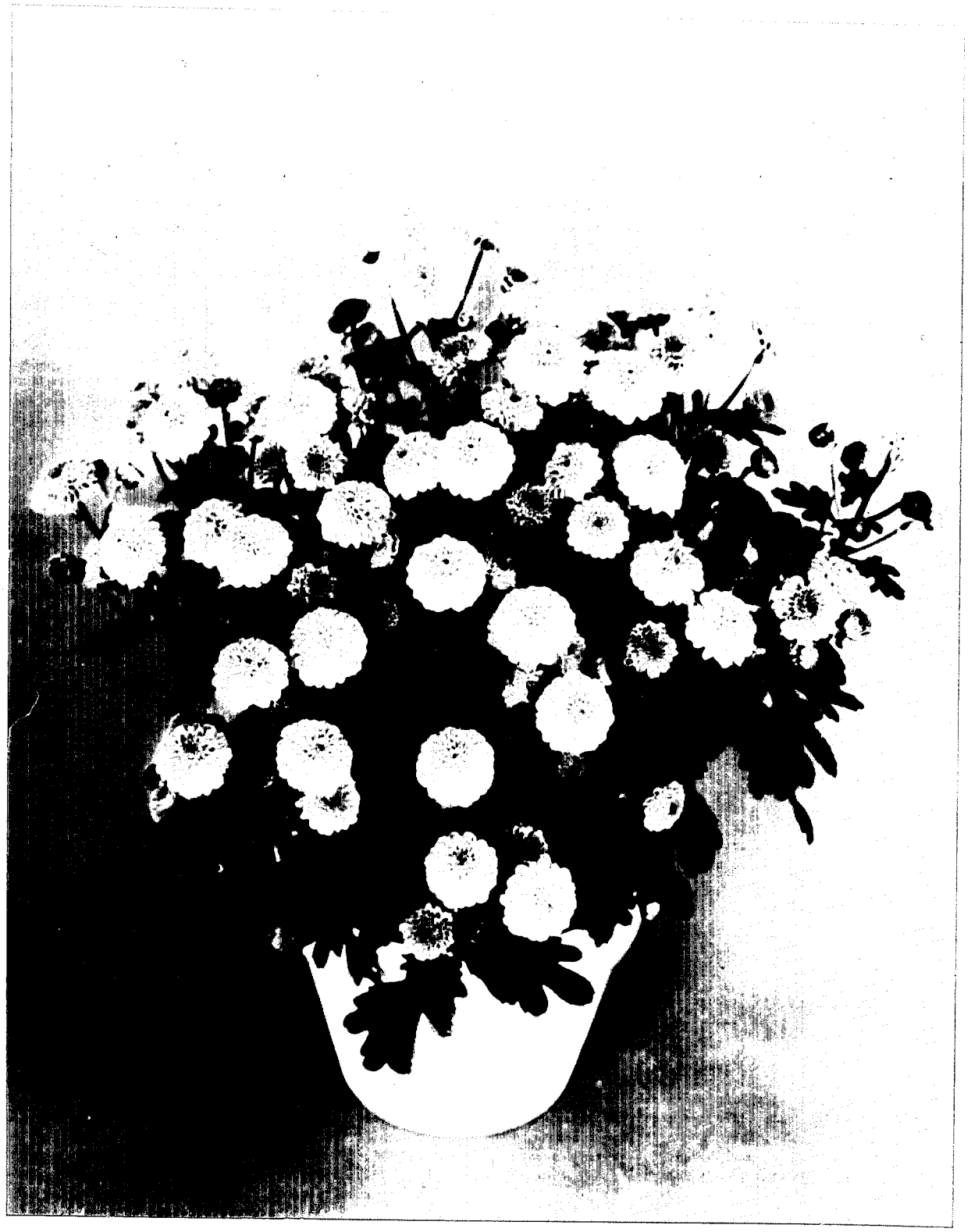

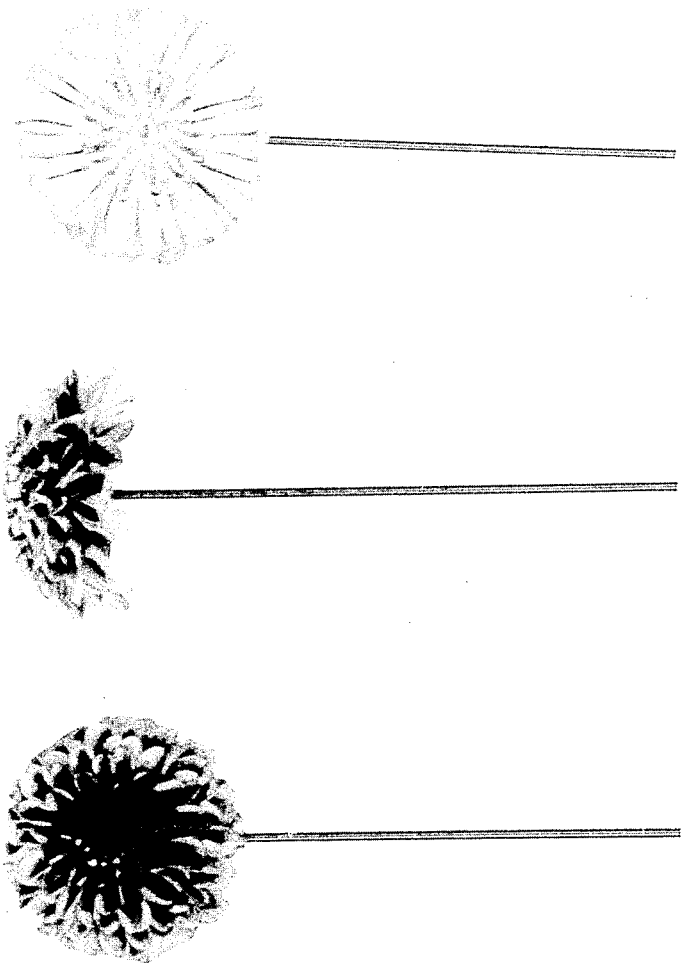

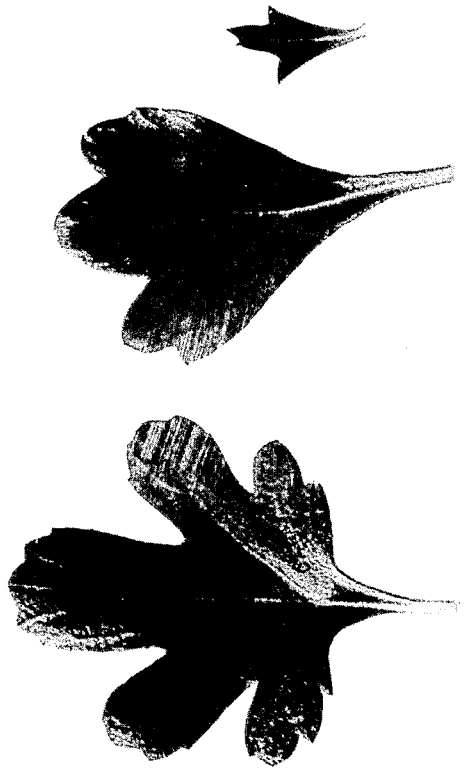

* * * * *